US010238864B2

(12) United States Patent
Anderson et al.

(10) Patent No.: US 10,238,864 B2
(45) Date of Patent: Mar. 26, 2019

(54) INTERVENTIONAL MEDICAL SYSTEMS AND ASSOCIATED TETHERING ASSEMBLIES AND METHODS

(71) Applicant: Medtronic, Inc., Minneapolis, MN (US)

(72) Inventors: Thomas A. Anderson, New Hope, MN (US); Vladimir Grubac, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 155 days.

(21) Appl. No.: 15/223,585

(22) Filed: Jul. 29, 2016

(65) Prior Publication Data
US 2018/0028805 A1    Feb. 1, 2018

(51) Int. Cl.
| | |
|---|---|
| A61N 1/05 | (2006.01) |
| A61N 1/375 | (2006.01) |
| A61N 1/362 | (2006.01) |
| A61B 1/04 | (2006.01) |
| A61B 17/04 | (2006.01) |
| A61B 17/34 | (2006.01) |
| A61N 1/372 | (2006.01) |

(52) U.S. Cl.
CPC ........ *A61N 1/0573* (2013.01); *A61B 17/0401* (2013.01); *A61B 17/3468* (2013.01); *A61N 1/362* (2013.01); *A61N 1/3756* (2013.01); *A61N 1/37205* (2013.01); *A61B 2017/0429* (2013.01); *A61B 2017/0464* (2013.01)

(58) Field of Classification Search
CPC .... A61N 1/0573; A61N 1/0587; A61N 1/362; A61N 1/37205; A61N 1/3756; A61B 17/3468
See application file for complete search history.

(56) References Cited

U.S. PATENT DOCUMENTS

| | | | |
|---|---|---|---|
| 5,350,397 | A | 9/1994 | Palermo et al. |
| 6,277,125 | B1 | 8/2001 | Barry et al. |
| 7,344,553 | B2 | 3/2008 | Opoloski et al. |
| 7,473,266 | B2 | 1/2009 | Glaser |
| 7,650,186 | B2 | 1/2010 | Hastings et al. |

(Continued)

OTHER PUBLICATIONS

Kelly, "Interventional Medical Systems, Associated Assemblies and Methods", U.S. Appl. No. 14/926,827, filed Oct. 29, 2015, 40 pages.

(Continued)

*Primary Examiner* — Tuan V Nguyen

(57) ABSTRACT

In an interventional medical system, a delivery catheter for deploying a medical device of the system has a tethering assembly that includes a tether line, a grip member, and a release member, wherein the tether line extends through a longitudinal lumen of a base of the release member and is coupled to a base of the grip member, and the release member has legs extending though apertures formed through the base of the grip member. The device may be tethered to the catheter such that a proximal end of the device is held within a cavity defined by a plurality of elastic fingers of the grip member that extend distally from the base thereof; and the device may be deployed from the catheter by moving the legs of the release member within the grip member cavity to push the proximal end of the device out from the cavity.

17 Claims, 7 Drawing Sheets

(56) References Cited

U.S. PATENT DOCUMENTS

| | | |
|---|---|---|
| 8,231,271 B2 | 7/2012 | Lane et al. |
| 8,364,280 B2 | 1/2013 | Marnfeldt et al. |
| 8,504,156 B2 | 8/2013 | Bonner et al. |
| 8,615,310 B2 | 12/2013 | Khairkhahan et al. |
| 8,777,932 B2 | 7/2014 | Sage et al. |
| 2009/0204170 A1* | 8/2009 | Hastings .............. A61N 1/0565 607/33 |
| 2012/0172690 A1 | 7/2012 | Anderson et al. |
| 2013/0053921 A1 | 2/2013 | Bonner et al. |
| 2013/0253344 A1 | 9/2013 | Griswold et al. |
| 2013/0253345 A1 | 9/2013 | Griswold et al. |
| 2014/0180306 A1 | 6/2014 | Grubac et al. |
| 2014/0200462 A1 | 7/2014 | Stalker et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0094668 A1 | 4/2015 | Wood et al. |
| 2016/0015968 A1 | 1/2016 | Bonner et al. |

OTHER PUBLICATIONS

Kelly, "Interventional Medical Systems, Associated Methods", U.S. Appl. No. 14/942,609, filed Nov. 16, 2016, 48 pages.
(PCT/US2017/044305) PCT Notification of Transmittal of the International Search Report and the Written Opinion of the International Searching Authority, dated Oct. 5, 2017, 15 pages.

\* cited by examiner

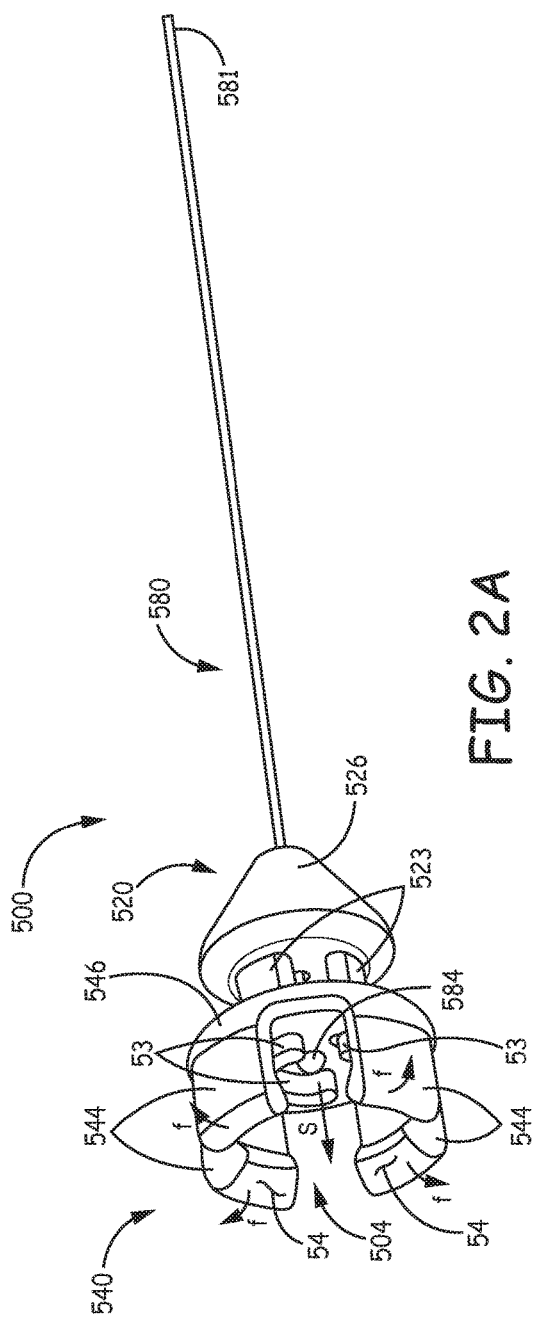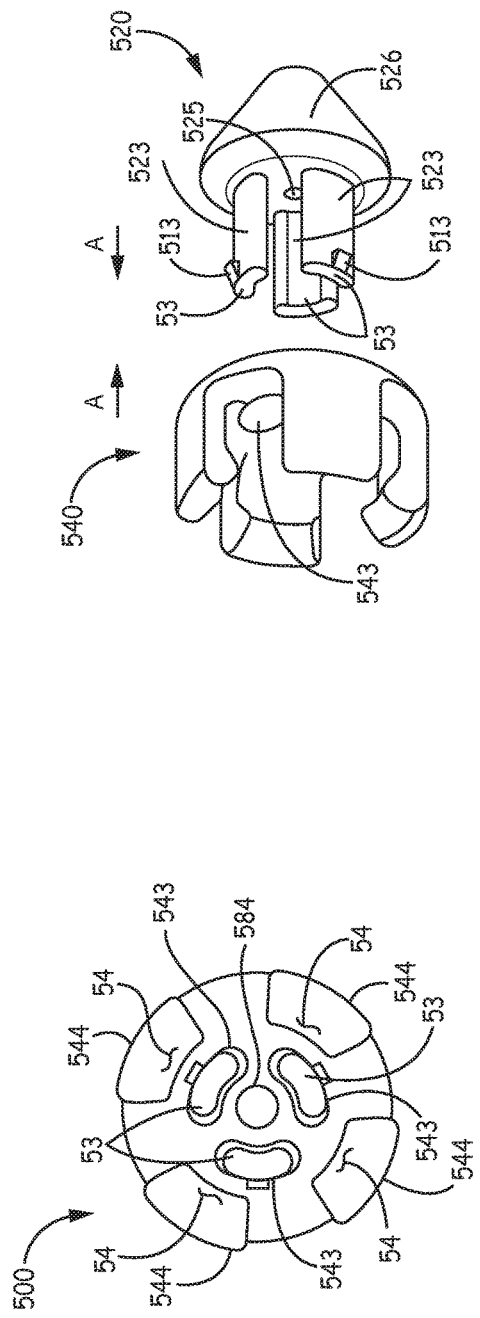

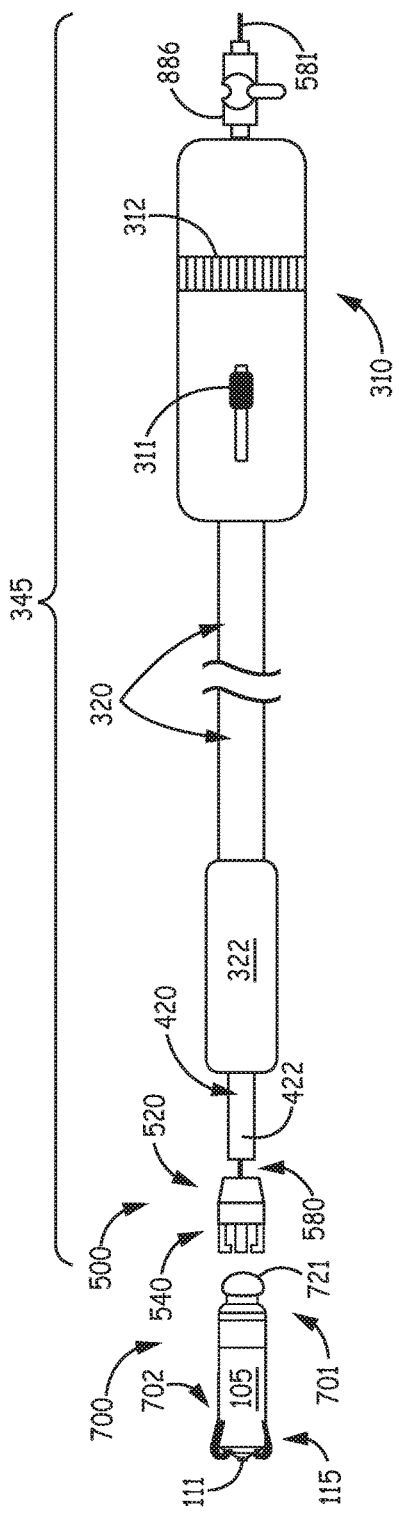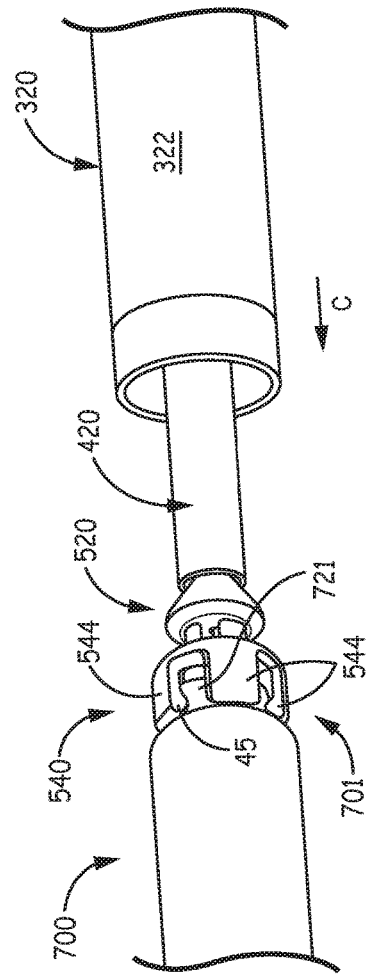
FIG. 3A
FIG. 3B

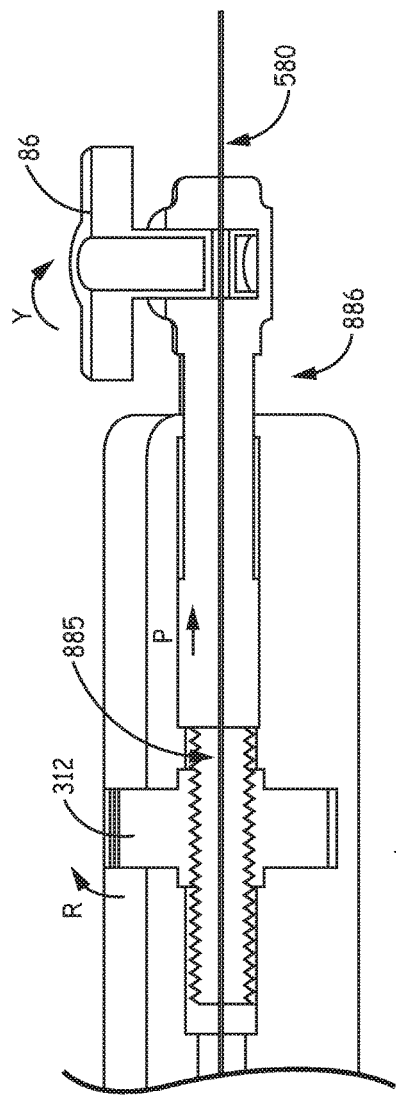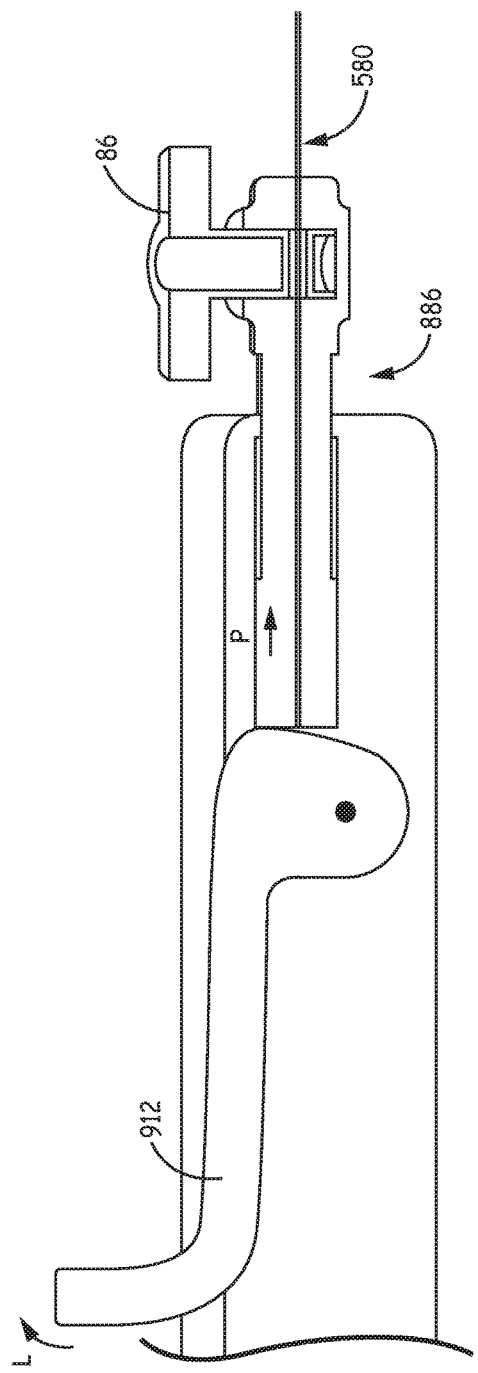

US 10,238,864 B2

INTERVENTIONAL MEDICAL SYSTEMS AND ASSOCIATED TETHERING ASSEMBLIES AND METHODS

FIELD OF THE DISCLOSURE

The present disclosure pertains to interventional medical systems, and more particularly to associated tethering assemblies and methods.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed housing 105, preferably formed from a biocompatible and biostable metal such as titanium, contains an electronic controller and associated power source (not shown), to which at least one electrode 111 is coupled, for example, by a hermetic feedthrough assembly (not shown) like those known to those skilled in the art. Housing 105 may be overlaid with an insulative layer, for example, medical grade polyurethane, parylene, or silicone, and a portion of the insulation layer may be removed to form another electrode 112, for example, which provides bipolar pacing and sensing in conjunction with electrode 111.

FIG. 1 shows device 100 having been deployed by an operator out from a distal opening 203 of a delivery catheter 200, which the operator has maneuvered up through the inferior vena cava IVC and across the right atrium RA into the right ventricle RV. The deployed device 100 is shown fixed at an implant site by a fixation member 115 thereof, but still secured to catheter 200 by a tether 280 that extends out from distal opening 203 of catheter 200.

Securing device 100 to catheter 200 with tether 280 is typically accomplished by looping tether 280 through an attachment feature 121 of device 100 and threading first and second lengths 281, 282 of tether 280 through one or more lumens of catheter 200 such that opposing ends thereof protrude out from a proximal opening 201 of catheter 200. After deploying device 100, the operator can grasp the ends of lengths 281, 282 and tug on tether 280, for example, to test the fixation of device 100 at the implant site, and/or to apply a greater force to tether 280 to remove device 100 from the implant site for repositioning at a more suitable site, if necessary. If satisfied with the implant of device 100, the operator can un-tether device 100 from catheter 200 by releasing, for example, the end of tether length 281, and then pulling on the end of the other tether length 282, thereby withdrawing an entirety of length 282 proximally through delivery catheter 200 so that the other length 281 is pulled distally and through device tether attachment feature 121, out from engagement therewith.

SUMMARY

The present disclosure pertains to improved apparatus and methods related to the tethering of implantable medical devices. According to some embodiments, in an interventional medical system, a delivery catheter for deploying a medical device of the system has a tethering assembly that includes a tether line, a grip member, and a release member, wherein the tether line extends through a longitudinal lumen of a base of the release member and is coupled to a base of the grip member, and the release member has legs extending though apertures formed through the base of the grip member. The device may be tethered to the catheter such that a proximal end of the device is held within a cavity of the tethering assembly grip member, which is defined by a plurality of elastic fingers of the grip member that extend distally from the grip member base; and the device may be deployed from the catheter by moving the legs of the tethering assembly release member within the grip member cavity to push the proximal end of the device out from the grip member cavity.

According to some embodiments and methods, the tethering assembly tether line extends within an elongate tubular member of the delivery catheter, and the tubular member is configured so that a distal end thereof can abut the tethering assembly release member to provide a backup force when increased tension in the tether line pulls the tethering assembly grip member proximally relative to the release member to push the device out from the cavity by moving the legs of the release member within the grip member cavity. A handle assembly of the delivery catheter, which is coupled to the tubular member, may include a locking member for securing the tethering assembly tether line, wherein the locking member may be moveable relative to the tubular member to vary the tension in the tether line, when the tether line is locked therein.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 2A is a perspective view of a tethering assembly for a delivery catheter, according to some embodiments;

FIG. 2B is an end view of the tethering assembly, according to some embodiments;

FIG. 2C is an exploded perspective view of a portion of the tethering assembly, according to some embodiments;

FIG. 3A is a plan view of an interventional medical system, according to some embodiments;

FIG. 3B is a perspective view of a portion of the system, according to some embodiments;

FIG. 5A is a cross-section view through a portion of a handle assembly of the system delivery catheter, according to some embodiments; and FIG. 5B is a schematic representation of a portion of a handle assembly, which may be employed by some alternate embodiments of the delivery catheter.

DETAILED DESCRIPTION

Figure 1:
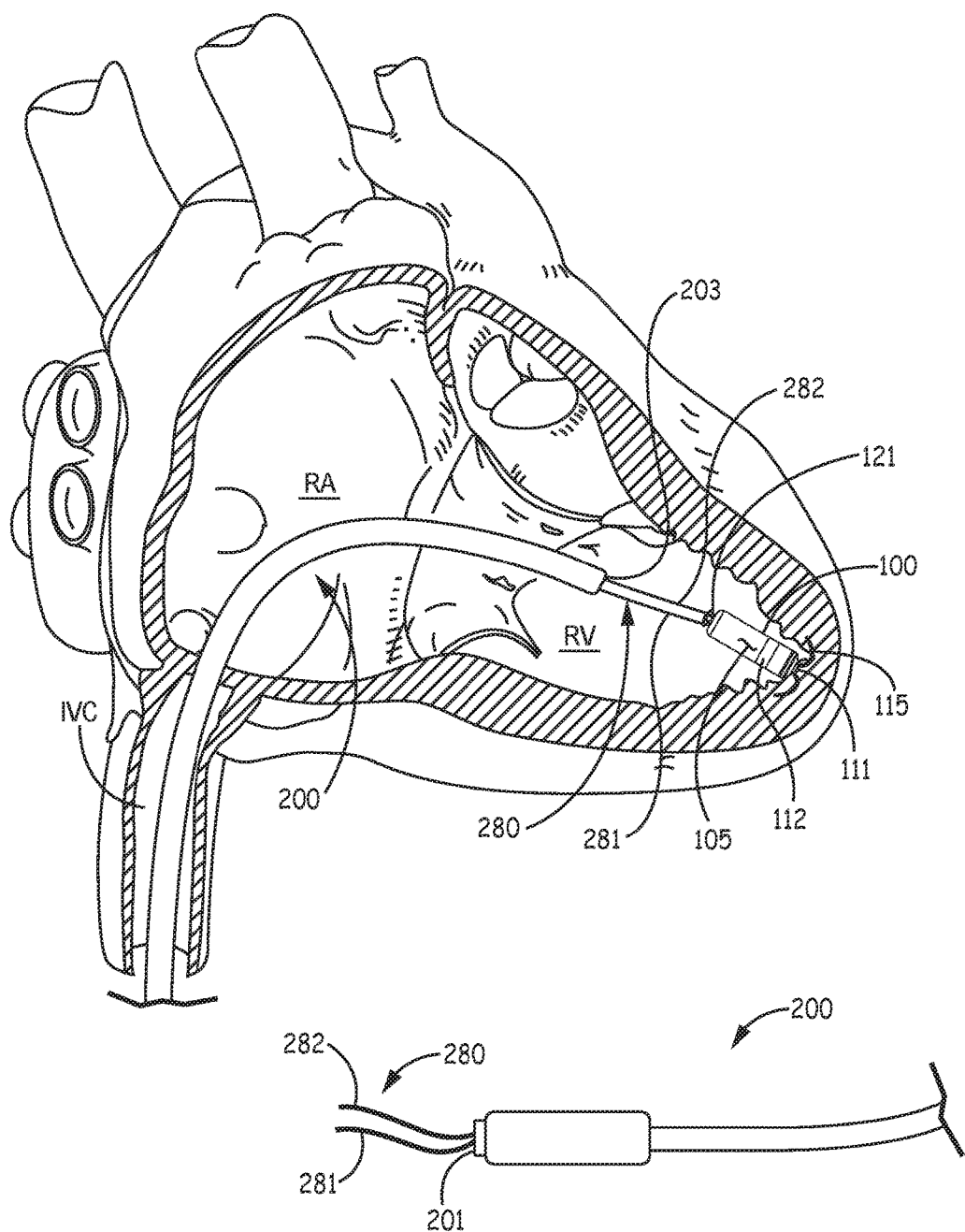
FIG. 1 is a schematic showing an exemplary implant of a relatively compact medical device, via an exemplary delivery catheter.

The following detailed description is exemplary in nature and is not intended to limit the scope, applicability, or configuration of the invention in any way. Rather, the following description provides practical examples, and those skilled in the art will recognize that some of the examples may have suitable alternatives.

FIGS. 2A-B are a perspective view and an end view of a tethering assembly 500, according to some embodiments, for example, that may be part of a delivery catheter 345 in a system described below in conjunction with FIGS. 3A-C. FIGS. 2A-B illustrates tethering assembly 500 including a tether line 580, a grip member 540, and a release member 520, wherein tether line 580 has a distal end 584 that is coupled to a base 546 of grip member 540, and tether line 580 extends proximally from distal end 584 through a longitudinal lumen 525 of release member 520, which is better seen in FIG. 2C. FIG. 2A further illustrates grip member 540 including a plurality of elastic fingers 544 extending distally from grip member base 546 and being spaced apart from one another around a plurality of apertures 543 that are formed through base 546. In FIGS. 2A-B, each of a plurality of legs 523 of release member 520 are shown extending from a base 526 of release member 520 and through a corresponding aperture 543 of grip member 540. According to the illustrated embodiment, grip member fingers 544 define a cavity 504 of grip member 540, which is sized to hold a proximal end of an implantable medical device, for example, as described below in conjunction with FIG. 3B.

FIG. 2C is an exploded perspective view of grip member 540 and release member 520. FIG. 2C illustrates grip and release members 540, 520 positioned for assembly together, per arrow A, wherein a distal end 53 of each leg 523 includes a barb-like projection 513 that has a tapered leading edge, to allow passage of each distal end 53 through the corresponding aperture 543 in the distal direction, per arrow A. According to the illustrated embodiment, once distal end 53 of each release member leg 523 passes through the corresponding grip member aperture 543, a trailing shoulder of each barb-like projection 513 secures release member 520 to grip member 540 by abutting grip member base 546, for example, as shown in FIGS. 2B and 3C. According to the illustrated embodiment, each release member leg 523 is in sliding engagement within the corresponding grip member aperture 543 to move, per arrow S, from a first position (shown) to a second position within cavity 504. When release member legs 523 are in the first position, the aforementioned proximal end of the medical device and distal ends 53 of legs 523 fit within grip member cavity 504.

According to an exemplary embodiment, grip member 540 and release member 520 are each molded from a relatively rigid medical grade plastic, examples of which include, without limitation, nylon, PEEK, ABS, and polyurethane; and tether line 580 is formed from a polyester fiber, which may have a fluoropolymer coating, in some embodiments. A knot in tether line distal end 584, or a bead-like member attached to distal end 584, may help to secure tether line 580 to grip member 540.

Figure 3C:
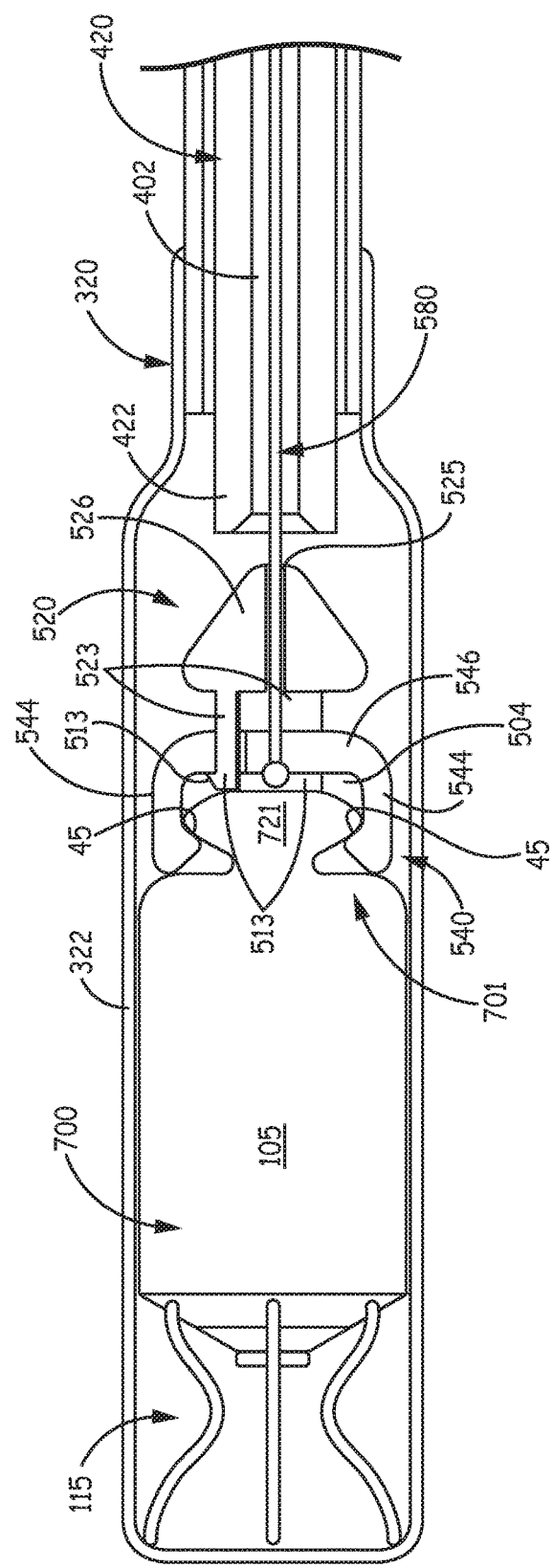
FIG. 3C is a plan view of the portion of the system, with a cut-away cross-section through a delivery catheter of the system, according to some embodiments.

FIG. 3A is a plan view of an interventional medical system that includes an implantable medical device 700 and the aforementioned delivery catheter 345 for deploying device 700, according to some embodiments. Like device 100, described above in conjunction with FIG. 1, device 700 includes an electronic controller and associated power source (not shown) contained in hermetically sealed housing 105, wherein electrode 111, being mounted to housing 105 at a distal end 702 of device 700, is electrically coupled to the controller, for example, by any suitable type of hermetically sealed feedthrough assembly known to those skilled in the art. Also like device 100, a portion of the insulation layer overlaying housing 105 of device 700 may be removed to form another electrode 112, for example, to provide bipolar pacing and sensing in conjunction with electrode 111. FIG. 3A illustrates catheter 345 including tethering assembly 500 and an elongate tubular member 420, which has a lumen 402 (FIGS. 3C, 4A-B) within which tether line 580 of assembly 500 extends so that grip and release members 540, 520 of tethering assembly 500 are located distal to a distal end 422 of tubular member 420. Tubular member 420 may zo be formed, for example, by extrusion, from any suitable medical grade polymer such as polyether block amide. According to the illustrated embodiment, a proximal end (not shown) of tubular member 420 is coupled to a handle assembly 310 of catheter 345, and a proximal end 581 of tether line 580 extends proximally out from handle assembly 310. FIG. 3A further illustrates catheter 345 including an outer shaft 320, which is slideably engaged around tubular member 420 and tethering assembly 500, and is coupled to a control member 311 of handle assembly 310, which is operable to move outer shaft 320 relative to tubular member 420 and tethering assembly 500. According to an exemplary embodiment, outer shaft 320 of catheter 345 may be constructed in a similar fashion to a deployment tube of a tool described in co-pending and commonly assigned U.S. Patent Application US 2015/0094668, Ser. Pat. No. 14/039,937 .

FIG. 3A shows outer shaft 320 in a retracted position with grip and release members 540, 520 of tethering assembly 500 exposed for insertion of a proximal end 701 of device 700 into grip member cavity 504 (FIG. 2A). According to the illustrated embodiment, a proximal end 701 of device 700 includes a knob-like member 721, which an operator can insert into grip member cavity 504 by pushing member 721 against inward tapering distal-facing surfaces 54 of grip member fingers 544 (FIGS. 2A-B) to elastically deform fingers 544, per arrows f, of FIG. 2A. Thus, device proximal end 701 can be held by grip member fingers 544 within cavity 504 so that proximal-facing surfaces 45 of grip member fingers 544 abut knob-like member 721, as shown in FIGS. 3B-C. The cut-away cross-section of FIG. 3C illustrates the aforementioned first position of tethering assembly release member legs 523, at which knob-like member 721 of device proximal end 701 and distal ends 53 of legs 523 both fit within grip member cavity 504. Proximal facing surfaces 45 of grip member fingers 544 are oriented to provide a sufficient holding force that keeps device 700 tethered to catheter 345, until the operator takes steps to release/deploy device 700, for example, as described below. (In addition to the orientation of surfaces 45, a thickness of each finger 544 factors into the holding force.)

With further reference to FIG. 3B, when device proximal end 701 is held by grip member fingers 544, the operator can complete the loading of device 700 into catheter 345 by moving outer shaft 320, per arrow C, for example, via control member 311 (FIG. 3A), so that a distal-most portion 322 of shaft 320 contains device 700, for example, as shown in FIG. 3C. According to the illustrated embodiment, when the operator advances outer shaft 320 over device 700 a plurality of elastic fixation fingers of fixation member 115 are moved from a relaxed condition (FIG. 3A) to an extended condition (FIG. 3C). Fixation member 115 may be cut from Nitinol tubing, according to methods known in the art, and fixation member 115 may be mounted to device housing 105 in a manner similar to that described for a fixation component in co-pending and commonly assigned U.S. patent application Ser. No. 2012/0172690. The superelastic nature of Nitinol allows the fingers of fixation member 115 to elastically deform between the relaxed and extended conditions.

Figure 4A:
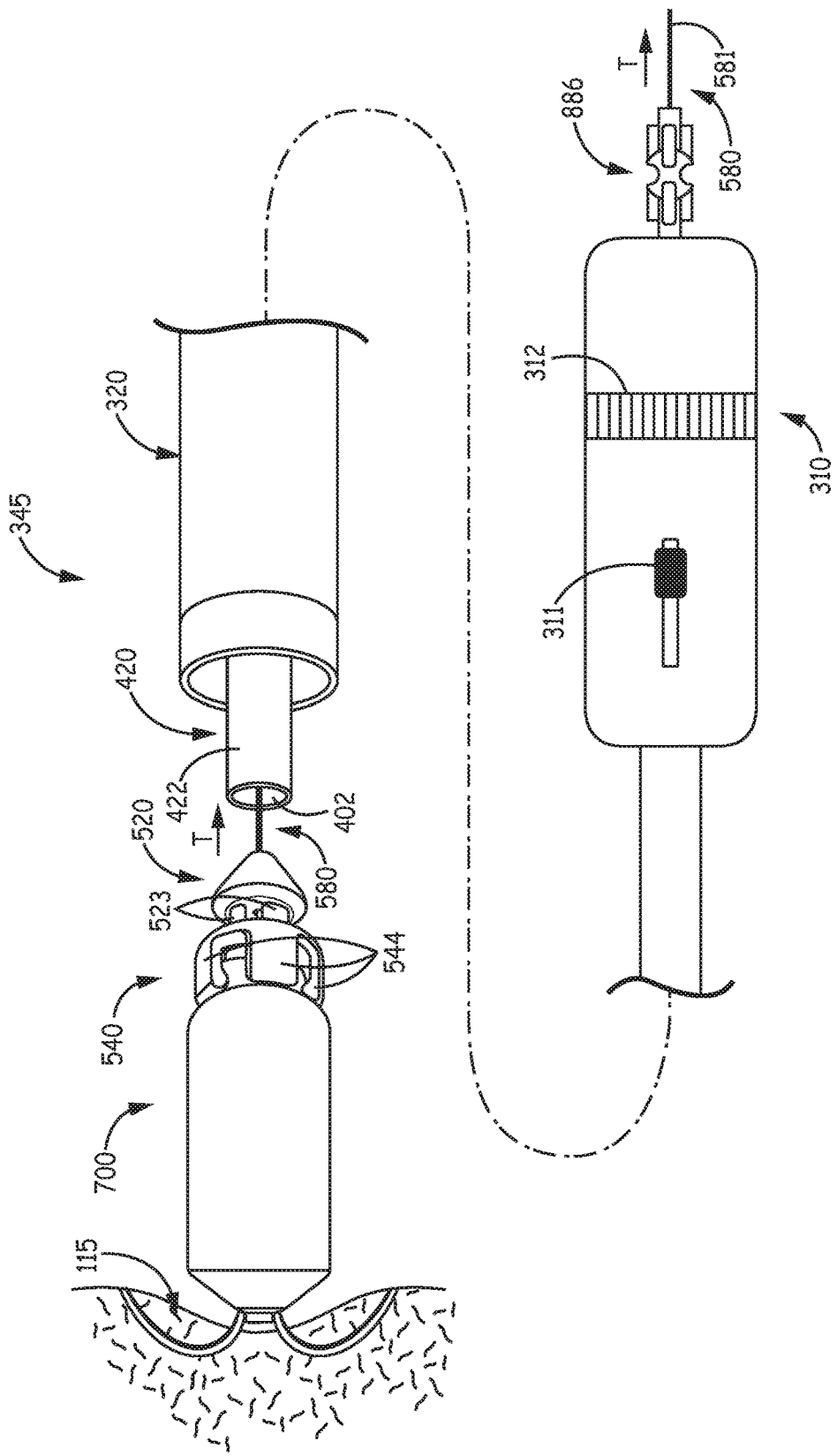
FIG. 4A is a schematic pertaining to methods for deploying an implantable medical device from the delivery catheter of the system, according to some embodiments.

FIG. 4A is a schematic pertaining to methods for deploying an implantable medical device, for example, device 700 from delivery catheter 345, according to some embodiments. FIG. 4A illustrates fixation member 115 of device 700 engaged with tissue at an implant site, for example, within a patient's right ventricle RV (FIG. 1). Prior to retracting outer shaft 320 relative to the tethered device 700 and tubular member 420, to engage fixation member 115, the operator has advanced catheter 345, for example, in the patient's venous system, and maneuvered outer shaft distalmost portion 322 into proximity with the implant site. According to some methods, the operator can test the fixation of engaged device fixation member 115, by applying a tug force to grip member 540, through tether line 580. In FIG. 4A, tether line proximal end 581 is shown extending out from a reversible locking member 886 of handle assembly 310. In FIG. 4A locking member 886 is unlocked to allow the operator to tug, per arrow T, on tether line proximal end 581. According to an exemplary embodiment, locking member 886 is in the form of a stopcock-type valve, known to those skilled in the art, which includes a controller 86 for alternately opening and constricting a lumen of locking member 886 through which tether line 580 passes. Grip member fingers 544 are configured, as described above, to hold device proximal end 701 in grip member cavity 504, until device proximal end 701 is pushed out from grip member cavity 504 by moving release member legs 523 within cavity 504 to the second position (shown in FIG. 4B). In FIG. 4A, release member 520 is not impinged upon by any force to move legs 523 relative to grip member 540 when the operator applies the tug force to test the fixation of engaged device fixation member 115.

Figure 4B:
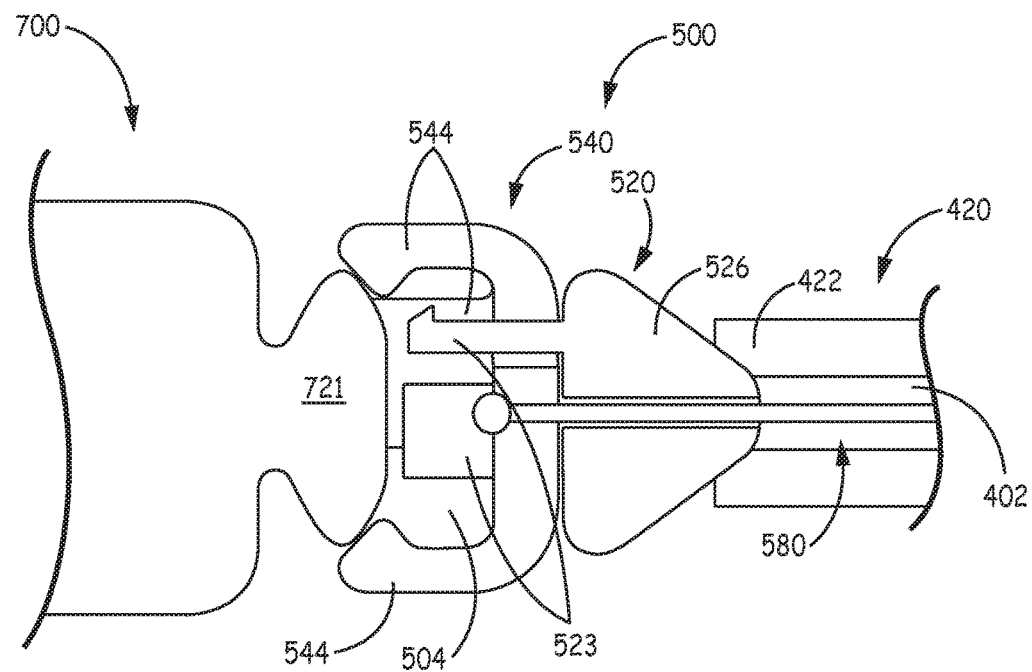
FIG. 4B is a cross-section view through a portion of the system when a release member of a tethering assembly of the delivery catheter has been moved to a second position, according to some embodiments and methods.

FIG. 4B is a cross-section view through a portion of the system, when the operator, satisfied with the implant of device 700, has taken steps to move release member 520 to the second position, thereby releasing/deploying device 700. FIG. 4B illustrates catheter tubular member 420 having been advanced relative to tethering assembly 500, so that tubular member distal end 422 abuts release member base 526. According to the illustrated embodiment, the abutting distal end 422 provides a back-up force for the operator to increase a tension in tether line 580 and pull grip member 540 proximally relative to release member 520, thereby moving release member legs 523 to the second position. FIG. 4B further illustrates release member base 526 having a tapered proximal end that can wedge within a distal opening of tubular member lumen 402 when distal end 422 provides the back-up force, according to some embodiments.

FIG. 5A is a cross-section view through a portion of catheter handle assembly 310, according to some embodiments. FIG. 5A illustrates the aforementioned reversible locking member 886 being coupled to an elongate threaded shaft 885, which extends within a shell of handle assembly 310, and has a lumen 805 in fluid communication with the lumen of locking member 886, through which tether line 580 extends. FIG. 5A further illustrates a thumbwheel type control member 312 of handle assembly 310 engaged with threaded shaft 885 to longitudinally move locking member 886 relative to tubular member 420. According to the illustrated embodiment, when tether line 580 is locked in locking member 886, for example, by rotating controller 86 of locking member 886, per arrow Y, and tubular member distal end 422 abuts release member base 526 (FIG. 4B), the operator can increase the tension in tether line 580 in a relatively steady and controlled fashion by rotating control member 312, per arrow R, to move locking member 886 proximally, per arrow P, and thereby release/deploy device 700 as described above. FIG. 5B is a schematic representation of a portion of a handle assembly that may be employed by some alternate embodiments of catheter 345. FIG. 5B illustrates the handle assembly including a cam action lever 912 engaged with locking member 886 to longitudinally move locking member 886, relative to tubular member 420, per arrow P, when lever 912 is lifted, per arrow L. Handle assembly embodiments may be constructed from injection molded, relatively hard, medical grade plastic parts, according to methods known in the art.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising an implantable medical device and a delivery catheter for deploying the device at an implant site, and the catheter comprising:

an elongate tubular member extending from a proximal end thereof to a distal end thereof, the tubular member including a lumen that extends from a proximal opening, at the proximal end, to a distal opening, at the distal end; and a tethering assembly comprising a tether line, a grip member, and a release member, the grip and release members being located distal to the distal end of the tubular member, the release member including a base, a longitudinal lumen extending through the base, and a plurality of legs extending distally from the base and being spaced apart from one another around the base lumen, the grip member including a grip member base, a plurality of apertures formed through the grip member base, and a plurality of elastic fingers extending distally from the grip member base and being spaced apart from one another around the plurality of apertures, each leg of the plurality of legs of the release member extending through a corresponding aperture of the grip member base and having a distal end configured to secure the release member to the grip member, the tether line extending through the lumens of the tubular and release members, being in sliding engagement within both lumens, and the tether line including a distal end coupled to the grip member base; and wherein the elastic fingers of the grip member define a cavity of the grip member, the cavity being sized to receive a proximal end of the device therein, the fingers being configured to hold the device proximal end within the cavity, and each finger being deformable to allow insertion and withdrawal of the device proximal end into and out from the cavity;

each leg of the release member extends into the grip member cavity and is in sliding engagement within the corresponding aperture of the grip member base to move from a first position in the cavity to a second position in the cavity, the first position at which the distal ends of the release member legs and the device proximal end both fit within the grip member cavity, and the second position at which the release member legs extend further into the grip member cavity so that the proximal end of the device does not fit therein; and the release member legs are moved from the first position to the second position when increased tension in the tether line pulls the grip member proximally relative to the release member.

2. The system of claim 1, wherein the tubular member of the catheter is configured so that the distal end thereof can abut the release member base to provide a backup force when the tension is increased in the tether line.

3. The system of claim 2, wherein the release member base of the catheter tethering assembly includes a tapered proximal end sized to wedge within the distal opening of the tubular member.

4. The system of claim 1, wherein the distal end of each release member leg of the catheter tethering assembly comprises a barb-like projection.

5. The system of claim 1, wherein the catheter further comprises a handle assembly coupled to the proximal end of the tubular member, the handle assembly including a reversible locking member through which a proximal end of the tethering assembly tether line extends, the locking member being longitudinally moveable relative to the tubular member, to vary the tension in the tether line when the proximal end of the tether line is locked in the locking member and the distal end of the tubular member abuts release member base of the tethering assembly.

6. The system of claim 5, wherein:
the catheter handle assembly further includes an elongate threaded shaft coupled to the locking member, the shaft having a lumen through which the tether line extends in proximity to the locking member; and
the catheter handle assembly further includes a thumb-wheel control member engaged with the threaded shaft to longitudinally move the locking member relative to the tubular member.

7. The system of claim 5, wherein the catheter handle assembly further includes a cam action lever engaged with the locking member to longitudinally move the locking member relative to the tubular member.

8. The system of claim 1, wherein the catheter further comprises an outer shaft slideably engaged around the tubular member, the outer shaft including a distal-most portion sized to contain the device therein, when the proximal end of the device is held in the grip member cavity by the grip member fingers of the catheter tethering assembly.

9. The system of claim 1, wherein the implantable medical device comprises an electronic controller and an associated power source, a hermetically sealed housing containing the controller and power source, an electrode electrically coupled to the controller and mounted to the housing, and a fixation member mounted to a distal end of the housing.

10. The system of claim 9, wherein the proximal end of the device comprises a knob-like member coupled to a proximal end of the housing thereof.

11. A tethering assembly for a delivery catheter, the catheter for deploying an implantable medical device at an implant site, and the assembly comprising:

a tether line extending from a proximal end thereof to a distal end thereof and being sized to fit in sliding engagement within a lumen of a tubular member of the delivery catheter;
a grip member including a grip member base, a plurality of apertures formed through the grip member base, and a plurality of elastic fingers extending distally from the base and being spaced apart from one another around the plurality of apertures, the grip member base being coupled to the distal end of the tether line; and
a release member including a base, a longitudinal lumen extending through the base, and a plurality of legs extending distally from the base and being spaced apart from one another around the release member lumen; and
wherein each leg of the plurality of legs of the release member extends through a corresponding aperture of the grip member base and has a distal end configured to secure the release member to the grip member;
the tether line extends through the lumen of the release member, being in sliding engagement therewith;
the elastic fingers of the grip member define a cavity of the grip member, the cavity being sized to receive a proximal end of the device therein, the fingers being configured to hold the device proximal end within the cavity, and each finger being deformable to allow insertion and withdrawal of the device proximal end into and out from the cavity;
each leg of the release member slides within the corresponding aperture of the grip member base to move within the grip member cavity from a first position to a second position, the first position at which the distal ends of the release member legs and the device proximal end both fit within the grip member cavity, and the second position at which the release member legs extend into the grip member cavity so that the proximal end of the device does not fit therein; and
the release member legs are moved from the first position to the second position when increased tension in the tether line pulls the grip member proximally relative to the release member.

12. The tethering assembly of claim 11, wherein the release member base includes a tapered proximal end sized to wedge within a distal opening of the lumen of the delivery catheter tubular member.

13. The tethering assembly of claim 11, wherein the distal end of each release member leg comprises a barb-like projection.

14. A method for deploying an implantable medical device from a delivery catheter, the device being tethered to the delivery catheter such that a proximal end of the device is held within a cavity of a grip member of a tethering assembly of the catheter, a base of the grip member being coupled to a distal end of a tether line of the tethering assembly that extends proximally therefrom and through a lumen of an elongate tubular member of the catheter, the grip member cavity being defined by a plurality of elastic fingers that extend distally from the grip member base; and the method comprising moving legs of a release member of the tethering assembly within the grip member cavity to push the proximal end of the device out from the grip member cavity, each leg of the release member extending though a corresponding aperture of a plurality of apertures formed through the grip member base.

15. The method of claim 14, wherein moving the legs of the tethering assembly release member comprises abutting a distal end of a tubular member of the catheter against the tethering assembly release member while increasing tension in the tethering assembly tether line to pull the tethering assembly grip member proximally relative to the release member.

16. The method of claim 15, wherein increasing tension in the tethering assembly tether line comprises:
   locking a proximal end of the tethering assembly tether line in a locking member of the catheter; and
   moving the locking member, with the tether line locked therein, proximally relative to the tubular member.

17. The method of claim 15, further comprising:
   advancing the catheter with the device tethered thereto into a body of a patient;
   maneuvering the distal-most portion of the advanced catheter into proximity with an implant site within the body of the patient;
   retracting an outer shaft of the catheter with respect to the tubular member of the catheter and the tethered device, to expose a fixation member of the device, while a distal end of the tubular member abuts the tethering assembly release member, so that the device fixation member engages with tissue at the implant site, the outer shaft being slideably engaged around the tubular member;
   withdrawing the catheter tubular member away from the tethering assembly release member so that the distal end thereof no longer abuts the release member of the engaged and tethered device; and
   testing a fixation of the engaged device fixation member by applying a tug force through the tethering assembly tether line, before moving the legs of the tethering assembly release member.

\* \* \* \* \*